United States Patent
Patil et al.

(10) Patent No.: US 11,549,076 B2
(45) Date of Patent: Jan. 10, 2023

(54) GLYCOL ETHER ESTER COMPOUNDS OF NEO-ALCOHOLS USEFUL IN LUBRICATING OIL COMPOSITIONS AND METHODS OF MAKING THE SAME

(71) Applicant: ExxonMobil Technology and Engineering Company, Annandale, NJ (US)

(72) Inventors: Abhimanyu O. Patil, Westfield, NJ (US); Satish Bodige, Wayne, NJ (US); Kyle G. Lewis, Houston, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 16/872,994

(22) Filed: May 12, 2020

(65) Prior Publication Data
US 2020/0399553 A1    Dec. 24, 2020

Related U.S. Application Data

(60) Provisional application No. 62/864,674, filed on Jun. 21, 2019.

(51) Int. Cl.
| | |
|---|---|
| C10M 105/34 | (2006.01) |
| C07C 67/08 | (2006.01) |
| C07C 69/708 | (2006.01) |
| C10N 20/02 | (2006.01) |
| C10N 20/00 | (2006.01) |
| C10N 40/25 | (2006.01) |

(52) U.S. Cl.
CPC ........... *C10M 105/34* (2013.01); *C07C 67/08* (2013.01); *C07C 69/708* (2013.01); *C10M 2207/2815* (2013.01); *C10N 2020/02* (2013.01); *C10N 2020/065* (2020.05); *C10N 2040/25* (2013.01)

(58) Field of Classification Search
None
See application file for complete search history.

(56) References Cited

U.S. PATENT DOCUMENTS

| | | | | |
|---|---|---|---|---|
| 10,662,388 B2 * | 5/2020 | Patil | ........................ | C07C 69/24 |
| 10,683,464 B2 * | 6/2020 | Patil | ...................... | C07C 69/007 |
| 10,711,216 B2 * | 7/2020 | Patil | ........................ | C07C 67/08 |
| 2016/0200998 A1 * | 7/2016 | Maruyama | ........... | C10M 129/70 508/100 |
| 2017/0183595 A1 * | 6/2017 | Ng | ........................ | C10M 105/34 |
| 2019/0100481 A1 * | 4/2019 | Patil | ...................... | C07C 31/125 |

OTHER PUBLICATIONS

A. O. Patil et al., "Ester Compounds, Lubricating Oil Compositions Containing Same and Process for Making Same", U.S. Appl. No. 62/551,068, filed Aug. 28, 2017.
A. O. Patil et al., "Ester Compounds, Lubricating Oil Compositions Containing Same and Process for Making Same", U.S. Appl. No. 62/565,536, filed Sep. 29, 2017.
A. O. Patil et al., "Ester Compounds, Lubricating Oil Compositions Containing Same and Process for Making Same", U.S. Appl. No. 62/565,548, filed Sep. 29, 2017.
A. O. Patil et al.,"Neo-Alcohol Compounds, Processes for Making Same and Use Thereof", U.S. Appl. No. 62/565,501, filed Sep. 29, 2017.

* cited by examiner

*Primary Examiner* — Amy C Bonaparte
(74) *Attorney, Agent, or Firm* — Robert A. Migliorini

(57) ABSTRACT

Compositions include ether ester compounds derived from neo-alcohols, lubricating oil base stocks containing such ester compounds, and lubricating oil compositions containing such ester compounds. Methods can include making and formulating compositions containing ether ester compounds derived from neo-alcohols.

23 Claims, No Drawings

US 11,549,076 B2

GLYCOL ETHER ESTER COMPOUNDS OF NEO-ALCOHOLS USEFUL IN LUBRICATING OIL COMPOSITIONS AND METHODS OF MAKING THE SAME

FIELD

The present disclosure relates to glycol ether ester compounds of neo-alcohols, base stocks and lubricating oil compositions comprising such compounds, and methods of making the same.

BACKGROUND

Polyalpha-olefins ("PAOs") are important lubricant base stocks with excellent lubricant properties, including high viscosity index ("VI"), low volatility and are available in various viscosity ranges (e.g., kinematic viscosity at 100° C. in the range of 2 to 300 cSt). However, PAOs are paraffinic hydrocarbons with low polarity. This low polarity leads to low solubility and dispersancy for polar additives or sludge generated during service. To compensate for this low polarity, lube formulators add one or multiple polar co-base stocks. For example, ester or alkylated naphthalene is often present at 1 to 50 wt % levels in many finished lubricant formulations to increase the fluid polarity which improves the solubility of polar additives and sludge.

Furthermore, fuel/energy efficiency has been identified as an important feature for lubricants. However, in order to provide step-out fuel economy while maintaining or improving other lubricant performance features, base stocks with lower friction coefficients are needed. Low friction coefficients and low viscosity at all temperature ranges are important properties which contribute to lubricant fuel economy.

Improving heat transfer is also an emerging need as the energy density of systems and equipment increases, where improving thermodynamic efficiency is often coupled with higher operating temperatures. There are also developing requirements to provide cooling fluids for hybrid and electric vehicles. Currently traditional cooling fluids, including formulated lubricants, can be used but have limited properties.

Therefore, need exists for cost-compatible, polar co-base stocks which improve solvency, have superior viscosity-volatility characteristics, exhibit suitable heat transfer fluid properties that meet industrial requirements for density, specific heat capacity, and thermal conductivity and can be used to formulate ultra-low viscosity oil lubricants for step-out fuel economy benefit.

SUMMARY

Glycol ether ester compounds synthesized from $C_{21}$ neo alcohol and glycol ethers have been found to be advantageously used in lubricating oil base stocks having desirable lubricating oil properties such as viscosity, volatility, polarity and oxidation stability.

Provided herein are a class of compounds defined by structural Formula F-I as follows:

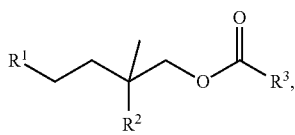

wherein: $R^1$ and $R^2$ are independently each a hydrocarbyl group containing at least 2 carbon atoms; and $R^3$ is a glycol ether or a polyglycol ether. In an aspect, $R^1$ and $R^2$ are each independently a C2 to C30 linear or branched alkyl group. In an aspect, at least one of $R^1$ and $R^2$ is a linear alkyl group. In an aspect, at least one of $R^1$ and $R^2$ is selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl. In an aspect, at least one of $R^1$ and $R^2$ is selected from n-butyl, n-hexyl, n-octyl, n-decyl, and n-dodecyl. In an aspect, $R^1$ and $R^2$ are independently each a linear alkyl group. In an aspect, $R^1$ and $R^2$ are independently selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl. In an aspect, at least one of $R^1$ and $R^2$ is a branched alkyl group. In an aspect, at least one of $R^1$ and $R^2$ is selected from ethylhexyl, 2-propylheptanyl, 2-butyloctyl, and 3,5-dimethyloctyl. In an aspect, $R^1$ and $R^2$ are the same.

In an aspect, $R^3$ is a glycol ether defined by the structural formula:

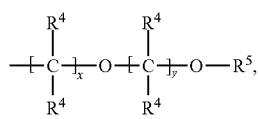

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, and y is a value from about 1 to about 10.

In an aspect, $R^3$ is a polyglycol ether defined by the structural formula:

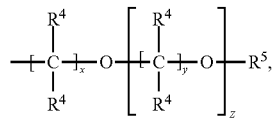

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, y is a value from about 1 to about 10, and z is a value from about 0 to about 100.

In an aspect, the compound of Formula F-I is 2-methyl-2-octyldodecyl 2-(2-methoxyethoxy) acetate or 2-methyl-2-octyldodecyl 2-(2-methoxyethoxy)ethoxyacetate.

Also, provided are lubricating oil compositions comprising one or more compounds of Formula F-I as described herein. In an aspect, the lubricating oil composition can be a lubricating oil base stock. In an aspect, the lubricating oil composition is a lubricating oil formulation.

Also, provided herein are methods for making an ester compound defined the structural Formula F-I

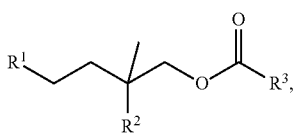

wherein: $R^1$ and $R^2$ are independently each a hydrocarbyl group containing at least two carbon atoms; and $R^3$ is a glycol ether or a polyglycol ether, the method comprising the steps of: providing a neo-alcohol compound defined by the structural Formula F-II as follows:

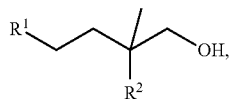

wherein $R^1$ and $R^2$ are the same as the $R^1$ and $R^2$ of Formula F-I, respectively; reacting the neo-alcohol with an acid compound defined by the structural Formula F-III as follows:

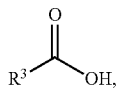

wherein $R^3$ is the same as the $R^3$ substituent group in Formula F-I, and/or an anhydride of the acid, in the presence of an acid catalyst to obtain a product mixture; and obtaining the ester compound and/or the lubricating oil base stock from the product mixture.

In an aspect, $R^1$ and $R^2$ are independently each a C2 to C30 linear or branched alkyl group. In an aspect, $R^1$ and $R^2$ are independently selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

In an aspect, $R^1$ and $R^2$ are identical. In an aspect, $R^3$ is a glycol ether defined by the structural formula:

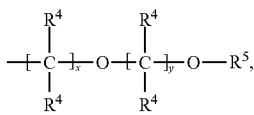

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10 and y is a value from about 1 to about 10.

In an aspect, $R^3$ is a polyglycol ether defined by the structural formula:

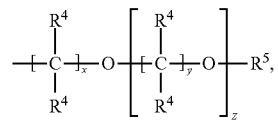

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, y is a value from about to about 10, and z is a value from about 0 to about 100.

DETAILED DESCRIPTION OF THE INVENTION

Definitions

In this disclosure, the indefinite article "a" or "an" means at least one, unless it is clearly specified or indicated by the context to mean one.

"Alkyl group" refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms.

"Cycloalkyl group" refers to an alkyl group in which all carbon atoms form a ring structure. Non-limiting examples of cycloalkyl groups include cyclopentyl, cyclohexyl, decahydronaphthalen-1-yl, spiro[5.5]undecan-3-yl, and the like.

"Aryl group" refers to an unsaturated, cyclic hydrocarbyl group consisting of carbon and hydrogen atoms in which the carbon atoms join to form a conjugated π system. Non-limiting examples of aryl groups include phenyl, 1-naphthyl, 2-naphthyl, 3-naphthyl, and the like.

"Arylalkyl group" refers to an alkyl group substituted by an aryl group or alkylaryl group. Non-limiting examples of arylalkyl group include benzyl, 2-phenylethyl, 4-phenylbutyl, and the like.

"Alkylaryl group" refers to an aryl group substituted by an alkyl group. Non-limiting examples of alkylaryl group include 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, and the like.

"Cycloalkylalkyl group" refers to an alkyl group substituted by a cycloalkyl group or an alkylcycloalkyl group. An example of cycloalkylalkyl group is cyclohexylmethyl, and the like.

"Alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tert-butylcyclohexyl, and the like.

"Glycol ether" refers to an ether group having a structure corresponding to the following formula:

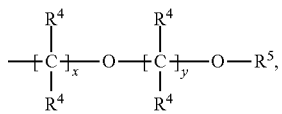

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, and y is a value from about 1 to about 10. "Polyglycol ether" refers to an ether group having a structure corresponding to the following formula:

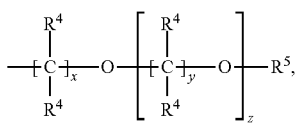

where each R4 is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), group (C4-C30), or arylalkyl group (C5-C30), x is a value from about 0 to about 10, y is a value from about 1 to about 10, and z is a value from about 0 to about 100.

"Hydrocarbyl group" refers to a group containing hydrogen and carbon atoms only. A hydrocarbyl group can be saturated or unsaturated, linear or branched, cyclic or acyclic, containing a cyclic structure or free of cyclic structure, and aromatic or non-aromatic. A "substituted" hydrocarbyl group is a hydrocarbyl group in which one or more hydrogen atom is substituted by any another group. An "unsubstituted" hydrocarbyl group is a hydrocarbyl group.

"Cn" group or compound refers to a group or a compound containing carbon atoms at total number thereof of n. Thus, "Cm-Cn" or "Cm to Cn" group or compound refers to a group or compound containing carbon atoms at a total number thereof in the range from m to n. Thus, a C1-C50 alkyl group refers to an alkyl group containing carbon atoms at a total number thereof in the range from 1 to 50.

"Mono-ester" refers to a compound having one ester (—C(O)—O—) functional group therein.

"Di-ester" refers to a compound having two ester (—C(O)—O—) functional groups therein.

"Gamma-branched alcohol' refers to an alcohol having a structure corresponding to the following formula:

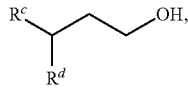

where $R^c$ and $R^d$ are independently any substituted or unsubstituted hydrocarbyl groups containing from d1 to d2 carbon atoms, where d1 and d2 can be, independently, 1, 2, 3, 4, 5, 6, 7, 8, 9, 10, 15, 20, 25, 30, 35, 40, 45, 50, 55, 60, 65, 70, 75, 80, 85, 90, 95, 100, as long as d1<d2. In an aspect, d1=2 and d2=50. In an aspect, $R^c$ and $R^d$ are alkyl groups. In an aspect, $R^c$ and $R^d$ are linear or branched alkyl groups. In an aspect, $R^c$ and $R^d$ differ in terms of total number of carbon atoms contained therein by two (2).

"Neo-acid" refers to a carboxylic acid having the following general structure:

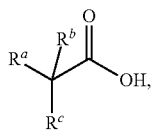

where $R^a$, $R^b$, and $R^c$ can be the same or different, and are independently selected hydrocarbyl groups.

"SAE" refers to SAE International, formerly known as Society of Automotive Engineers, which is a professional organization that sets standards for internal combustion engine lubricating oils.

"SAE J300" refers to the viscosity grade classification system of engine lubricating oils established by SAE, which defines the limits of the classifications in rheological terms only.

"Lubricating oil" refers to a substance that can be introduced between two or more surfaces and lowers the level of friction between two adjacent surfaces moving relative to each other. Non-limiting examples of lubricating oils include those in liquid form during normal use thereof such as engine oils and gear box oils and those in viscous liquid form during normal use such as grease. A lubricating oil "base stock" is a material, typically a fluid at various levels of viscosity at the operating temperature of the lubricating oil, used to formulate a lubricating oil by admixing with other components. Non-limiting examples of base stocks suitable in lubricating oils include API Group I, Group II, Group III, Group IV, and Group V base stocks. If one base stock is designated as a primary base stock in the lubricating oil, any additional base stock can be called a co-base stock.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

All Noack volatility ("NV") values in this disclosure are as determined pursuant to ASTM D5800 unless specified otherwise. Unit of all NV values is wt %, unless otherwise specified.

All percentages in describing chemical compositions herein are by weight unless specified otherwise. "Wt %" means percent by weight.

"Consisting essentially of" means containing at a concentration by weight of at least 90 wt %, based on the total weight of the mixture in question. Thus, a lubricating oil base stock consisting essentially of a given ester compound comprises that ester compound at a concentration by weight of at least 90 wt %, based on the total weight of the lubricating oil base stock.

All numerical values within the detailed description and the claims herein are modified by "about" or "approximately" the indicated value, taking into account experimental error and variations that would be expected by a person having ordinary skill in the art.

Neo-Alcohol-Derived Ester Compounds

Branched aliphatic primary alcohols, especially those having long carbon chains, have been found useful as an intermediate for making derivatives such as esters and ethers that can be used as base stocks and/or additives.

A specific type of branched aliphatic alcohols are Guerbet alcohols, which are beta-branched primary alcohols having the following general structure:

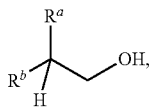

where $R^a$ and $R^b$ can be any hydrocarbyl group, preferably alkyl groups such as linear alkyl groups. Guerbet alcohol derivatives, such as esters, have found many useful such as lubricant base stocks. Guerbet alcohols can be produced by Guerbet reaction, in which two primary alcohol molecules condense to produce a beta-branched primary alcohol molecule and water.

A neo-alcohol having general structure

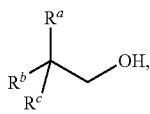

where $R^a$, $R^b$, and $R^c$ are independently hydrocarbyl groups, can have similar properties and uses of a Guerbet alcohol with similar molecular structure. Derivatives of neo-alcohols can find similar use to those of similar derivatives of Guerbet alcohols. Neo-alcohols and their derivatives can be particularly useful because of the presence of the quaternary carbon on the beta-location. Neo-alcohols comprising one or more long carbon chains having at least 6 carbons can be particularly interesting. Neo-alcohols are not made by Guerbet reaction.

Provided herein are compounds defined by the structural Formula F-I as follows:

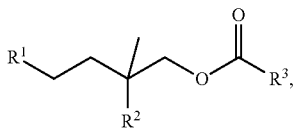

wherein $R^1$ and $R^2$ are each independently a hydrocarbyl group containing at least 2 carbon atoms therein, which can include a C2 to C60 hydrocarbyl group such as a C2 to C60 alkyl group, a C2 to C60 linear or branched alkyl group, or C2 to C30 linear or branched alkyl group; and $R^3$ is a glycol ether or polyglycol ether. To the extent this compound can be considered as an ester derived from a neo-alcohol, it will be referred to as such in this disclosure, and/or as an "ester of this disclosure" or "esters of this disclosure" herein.

In an aspect, $R^1$ and $R^2$ of Formula F-I each independently include c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or 60, as long as c1<c2. In an aspect, c1 and c2 can include range values selected from any one of c1=2 and c2=30, c1=2 and c2=24, c1=4 and c2=16, and c1=4 and c2=12. In an aspect, $R^1$ and $R^2$ each independently contain an even number of carbon atoms.

At least one of $R^1$ and $R^2$ (or both $R^1$ and $R^2$ independently each) can be a branched alkyl group, such as a branched alkyl group defined by the structural Formula F-IV:

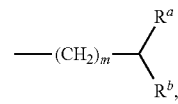

where $R^a$ and $R^b$ are independently hydrocarbyl groups, including alkyl groups such as linear or branched alkyl groups. In an aspect, $R^a$ and $R^b$ are linear alkyl groups. In an aspect, m is a non-negative integer, including a non-negative integer satisfying an inequality selected from any one of m≥2, m≥3, m≥4, m≥5, m≥6, and m≥7. In an aspect, $R^a$ and $R^b$ each independently include c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. In an aspect, c3 and c4 can be selected from any one of the following integer pairs: c3=1 and c4=50, c3=1 and c4=40, c3=1 and c4=20, c3=1 and c4=16, and c3=1 and c4=10. In an aspect, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (or both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. In an aspect, the total number of carbon atoms in linear $R^1$ and $R^2$ is an even number. In an aspect, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. In an aspect, the total number of carbon atoms in the linear $R^1$ and $R^2$ combined is within a range selected from any one of 8 to 96, 8 to 80, 8 to 64, 8 to 48, 8 to 40, 8 to 32, 8 to 28, 8 to 26, 8 to 24, 8 to 22, and 8 to 20.

In an aspect, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. In an aspect, the total number of carbon atoms in $R^1$ and $R^2$ is in a range selected from any one of 8 to 96, 8 to 80, 8 to 64, 8 to 48, 8 to 40, 8 to 32, 8 to 28, 8 to 26, 8 to 24, 8 to 22, and 8 to 20.

In an aspect, $R^1$ and $R^2$ can be identical. In an aspect, $R^1$ and $R^2$ can contain even number of carbon atoms. In an aspect, $R^1$ and $R^2$ can have identical linear alkyl groups. Where $R^1$ and $R^2$ in Formula F-I differ, it is highly desirable that they differ in terms of molar mass thereof by no greater than 145 (or 130, 115, 100, 85, 70, 55, 45, 30, or even 15) grams per mole. In an aspect, in such cases, $R^1$ and $R^2$ differ in terms of total number of carbon atoms contained therein by no greater than 10 (or 9, 8, 7, 6, 5, 4, 3, 2, or even 1).

In an aspect, $R^3$ can be a glycol ether having a structure corresponding to the following formula:

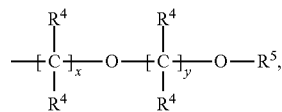

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), is hydrogen or a substituted or unsubstituted alkyl group (C1-C3)), alkenyl group (C1-C30), alkoxy group (C1-C30), aryl group (C4-C30), or arylalkyl group (C5-C30), x is a value from about 0 to about 10 and y is a value from about 1 to about 10.

In an aspect, $R^3$ can be a polyglycol ether having a structure corresponding to the following formula:

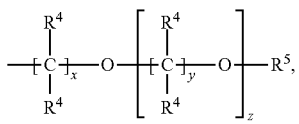

where each R is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C1-C30), or arylalkyl group (C5-C30), x is a value from about 0 to about 10, y is a value from about 1 to about 10, and z is a value from about 0 to about 100.

In an aspect, $R^3$ can include up to 60, 50, 40, 30, or 20 carbon atoms. In an aspect, $R^3$ is a C1-C24 group including carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2.

In an aspect, example of ester compounds which can be used alone or in combinations in a lubricating oil base stock formulation include 2-methyl-2-octyldodecyl 2-(2-methoxyethoxy)acetate, 2-ethyl-2-octyldodecyl 2-(2-methoxyethoxy)acetate, 2-methyl-2-hexyldecyl 2-(2-methoxyethoxy)acetate, 2-methyl-2-octyldodecyl 2-(2-ethoxyethoxy)acetate, 2-methyl-2-octyldodecyl 2-(3-methoxypropoxy)acetate, 2-methyl-2-octyldodecyl 3-(2-methoxyethoxy)propionate, 2-methyl-2-octyldodecyl 2-(2-(2-methoxyethoxy)ethoxy)acetate, 2-ethyl-2-octyldodecyl 2-(2-(2-methoxyethoxy)ethoxy)acetate, 2-methyl-2-hexyldecyl 2-(2-(2-methoxyethoxy)ethoxy)acetate, 2-methyl-2-octyldodecyl 2-(2-(2-ethoxyethoxy)ethoxy)acetate, 2-methyl-2-octyldodecyl 2-(2-(3-methoxypropoxy)ethoxy)acetate, 2-methyl-2-octyldodecyl 2-(3-(2-methoxyethoxy) propoxy)acetate, 2-methyl-2-octyldodecyl 3-(2-(2-ethoxyethoxy)ethoxy)propionate, and the like.

The present neo-alcohol-derived ether ester compounds can be used in a variety of applications, particularly as a base stock for lubricating oil compositions and can also be used in plasticizers, personal care products, heat transfer fluids, hydraulic power transfer oils, and processing oils.

The subject glycol ether ester compounds as a base stock offers an appropriate level of solubility and dispersancy for polar additives and/or sludge generated during service of lubricating oils as well as having high oxidation stability.

Specifically, in the present neo-alcohol-derived ether ester compounds, there is a quaternary carbon atom at the beta location to the ester group. Without intending to be bound by any theory, it is believed that the presence of this quaternary carbon leads to higher oxidation stability at high temperature of the molecule compared to a similar ester having a hydrogen atom ("beta-hydrogen") connected to the carbon atom at the beta location. The availability of a beta-hydrogen makes decomposition of the ester compound via a possible six-member ring mechanism (mechanism (a) below), which requires lower energy than the free-radical mechanism necessitated by the quaternary carbon in the neo-alcohol (mechanism (b) below).

(a) Decomposition via six-member ring mechanism

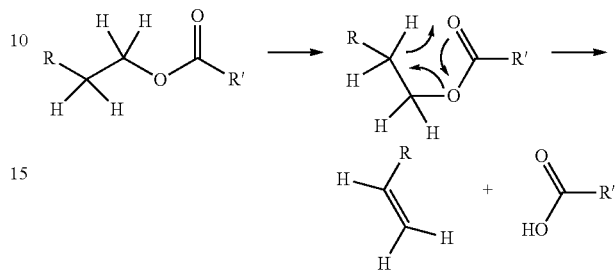

(b) Decomposition via free-radical mechanism

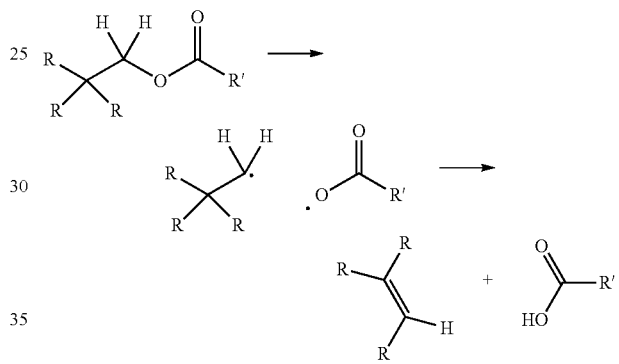

The present compounds can be a mono-ester derived from a mono neo-alcohol instead of a polyol. Compared to known esters derived from neo-polyols, a mono-ester derived from a mono neo-alcohol tends to have lower polarity. However, the ester group in the molecule imparts higher polarity to the esters of this disclosure than hydrocarbon molecules such as polyalphaolefins. Moderate polarity of a mono-ester can be particularly desirable for blending with polyalphaolefins and polar additives used in the present lubricating oil compositions.

Lubricating Oil Compositions Containing Esters

General

In this disclosure, a lubricating oil formulation means a lubricating oil product ready for its intended use. Thus, examples of lubricating oil formulations include: engine oils ready for putting into the crankcase of an internal combustion engine; gear oils ready for being dispensed into a gear box; greases ready for being applied to apparatus in need of greasing; and the like. In this disclosure, a lubricating oil composition can be any portion or the entirety of a lubricating oil formulation. Thus, a lubricating oil composition can be, for example: (i) a base stock; (ii) an additive package containing one or more additives; (ii) a mixture of two or more base stocks absent any additive; (iii) a mixture of one or more base stocks with one or more additives but not the entirety of a lubricating oil formulation; and (iv) a lubricating oil formulation in its entirety.

The present esters are useful as base stocks in formulating lubricating oil compositions. To make a final lubricating oil formulation as a product, one can add additional components, such as other base stocks, additional quantities of the materials already present in the lubricating oil composition, additional components, and the like, to the lubricating oil composition. In an aspect, the present lubricating oil composition can be a lubricating oil formulation.

Lubricating Oil Base Stocks Containing Neo-Alcohol-Derived Ester

Esters of neo-alcohols have desirable properties such as KV100, KV40, and viscosity index comparable to certain commercial Group V ester-type base stocks. The high polarity of the neo-alcohol-derived ester molecules as a result of the presence of the ester group lends them excellent blending capabilities with many other base stocks, providing needed solvency and dispersancy of polar components such as additives and sludge formed during the service life of the lubricating oil. The exceptionally high oxidation stability of the neo-alcohol-derived ester molecules as a result of the location of the ester group connected to a quaternary carbon atom with no hydrogen directly bonded thereto is particularly desirable for a high-performance lubricating oil formulation which is exposed repeatedly to oxidative environment such as automotive engine oils.

The present base stock (also referred to herein as "lubricating oil base stock") can comprise a single neo-alcohol-derived ester compound as disclosed above. The concentration of the ester compound in the base stock can be, e.g., at least 80, 90, 95, 98, or even 99 wt %, based on the total weight of the base stock.

The lubricating oil base stock can comprise two or more neo-alcohol-derived esters as disclosed above. Such base stock can be produced by mixing two ester compounds in their substantially pure form, or produced from a single esterification reaction operation by reacting (i) one neo-alcohol with two or more acids, or (ii) two or more neo-alcohols with one or more acids. Such mixed-ester base stock can be particularly advantageous where a mixture of neo-alcohols (including neo-alcohols with similar molecular weights and/or molecular structures) or a mixture of acids (including acids with similar molecular weights and/or molecular structures) can be procured at a lower cost than a pure single-compound neo-alcohol product or acid product.

The present lubricating oil base stock can have a KV100 in the range from $k1$ to $k2$ cSt, where $k1$ and $k2$ can be, independently, 1.0, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, as long as $k1<k2$. In an aspect, $k1=4.0$, and $k2=30.0$. In another aspect, $k1=5.0$, and $k2=25.0$. Therefore, the base stock of the present disclosure has a relatively "low" viscosity at the normal operating temperature of an internal combustion engine lubricating oil.

The lubricating oil base stock can have a viscosity index as determined pursuant to ASTM D2270 in the range from $v1$ to $v2$, where $v1$ and $v2$ can be, independently, −100, −90, −80, −70, −60, −50, −40, −30, −20, −10, 0, 10, 20, 30, 40, 50, 60, 70, 80, 90, 100, 110, 120, 130, 140, 150, 160, 170, 180, 190, 200, 210, 220, 230, 240, 250, 260, 270, 290, or 300, as long as $v1<v2$. In an aspect, $v1$ and $v2$ can be a pair of values selected from any one of $v1=0$ and $v2=250$, $v1=25$ and $v2=200$, and $v1=100$ and $v2=170$.

The present base stock can have a NV value in the range from $n1$ to $n2$ wt %, where $n1$ and $n2$ can be, independently, 0, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, or 90, as long as $n1<n2$. In an aspect, $n1$ and $n2$ can be a pair of values selected from any one of $n1=0$ and $n2=50$, $n1=0$ and $n2=30$, $n1=0$ and $n2=20$, and $n1=0$ and $n2=16$. In general, for the same type of gamma-branched alcohol-derived ester base stock, the larger the molecular weight of the molecule, the lower the NV value. For engine oils and base stocks containing a gamma-branched alcohol-derived ester, NV values can be lower than comparative engine oil and base stock formulations.

In an aspect, the present base stock can have an aniline value as determined by ASTM D611 of no higher than 30, 25, 20, or 15.

As discussed above, compared to ester base stocks derived from neo polyols, the present ester base stock (also referred to as "neo-alcohol-derived ether base stock," "base stock" and/or "lubricating oil base stock") contains mono neo-alcohol-derived esters and tends to have lower polarity, which is conducive to seal compatibility of lubricating oil compositions. On the other hand, due to the presence of the quaternary carbon atom in the esters of this disclosure, the ester base stock tends to have high oxidation stability, making it particularly desirable for lubricating oil compositions intended for high-temperature operation with exposure to oxygen.

The present neo-alcohol-derived ether ester base stock ("base stock") can be used as a primary base stock or a co-base stock in any lubricating oil formulation. In an aspect, the neo-alcohol-derived ester base stock of this disclosure is used as a co-base stock in conjunction with a second base stock designated as a primary base stock. In certain applications, two or more additional base stocks can be used in the lubricating oil formulation, in addition to the present neo-alcohol-derived ester base stock. The present base stock contains a neo-alcohol-derived ester and is particularly advantageous when used as a co-base stock with a non-polar base stock such as those Group I, II, III, GTL, and Group IV base stocks.

The present base stocks can be used for formulating automobile engine lubricating oils, including those meeting the SAE J300 classification standards. However, it is contemplated that the present base stocks can be used to formulate other lubricating oils (e.g., automobile drive-line oils, industrial lubricating oils, gear oils, greases, and the like), heat transfer oils (e.g., transformer oils), hydraulic power transfer oils, processing oils, and the like.

The present base stocks are useful in a lubricating oil formulation in an amount from about $c1$ to $c2$ wt %, based on the total weight of the lubricating oil composition, where $c1$ and $c2$ can be, independently, 1, 2, 3, 4, 5, 6, 7, 8, 9, 10, 15, 20, 25, 30, 35, 40, 45, 50, 55, 60, 65, 70, 75, 80, 85, 90, or 95, as long as $c1<c2$. In an aspect, $c1$ and $c2$ can be range limits selected from any one of $c1=3$ and $c2=50$, and $c1=5$ and $c2=30$. In general, it is desirable that the lubricating oil composition contains the neo-acid-derived ester base stock as a co-base stock. However, it is also contemplated that the present lubricating oil formulation can contain the neo-acid derived ester base stock as a primary base stock, and in an extreme case, the lubricating oil formulation can include mostly the neo-acid derived ester base stock and additives.

Owing to the high polarity of the neo-alcohol-derived ester base stocks resulting from the ester group in their molecular structures, the present lubricating oil compositions can have an improved additive and sludge solvency and dispersancy compared to other lubricating oil compositions free of ester-type base stocks. In addition, a lubricating oil composition including a neo-alcohol-derived ester base stock can have improved seal compatibility compared to compositions free of ester-type base stocks. Moreover, owing to the presence of the quaternary carbon atom in the molecule structure, the neo-alcohol-derived ester base stock of this disclosure can have a high thermal stability.

Other Base Stocks Useful in the Lubricating Oil Compositions

A wide range of lubricating oil base stocks known can be used together with the present neo-alcohol-derived ester base stock in the lubricating oil compositions, as a primary base stock or a co-base stock. Such other base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve the at least one lubricating oil property. Re-refined oil base stocks are obtained by processes analogous to refined oils but using an oil that has been previously used as a feed stock.

API Groups I, II, III, IV and V are broad categories of base stocks developed and defined by the American Petroleum Institute (API Publication 1509; www.API.org) to create guidelines for lubricating oil base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group IV includes polyalphaolefins (PAO). Group V base stocks include base stocks not included in Groups I-IV. Table 1 summarizes properties of each of these five groups.

TABLE 1

Base Stock Properties

| | Saturates | Sulfur | Viscosity Index |
|---|---|---|---|
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | | PAO products | |
| Group V | All other products not included in Groups I, II, III, and IV | | |

Natural oils include animal oils (e.g., lard), vegetable oils (e.g., castor oil), and mineral oils. Animal and vegetable oils possessing favorable thermal oxidation stability can be used. Mineral oils vary widely as to their crude source, e.g., as to whether they are paraffinic, naphthenic, or mixed paraffinic-naphthenic. Oils derived from coal or shale are also useful in this disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalpha-olefins ("PAOs") base stocks are placed into Group IV. Advantageous Group IV base stocks are those made from one or more of C6, C8, C10, C12, and C14 linear alpha-olefins ("LAO"s). These base stocks can be commercially available at a wide range of viscosity, such as a KV100 in the range from 1.0 to 1,000 cSt. The PAO base stocks can be made by polymerization of the LAO(s) in the presence of Lewis-acid type catalyst or a metallocene compound-based catalyst system. High quality Group IV PAO commercial base stocks include the SpectraSyn™ and SpectraSyn Elite™ series available from ExxonMobil Chemical Company having an address at 4500 Bayway Drive, Baytown, Tex. 77520, United States.

All other synthetic base stocks, including but not limited to alkyl aromatics and synthetic esters are in Group V.

Additional esters not in the neo-alcohol-derived ester category in a minor amount can be useful in the present lubricating oil compositions. Additive solvency and seal compatibility characteristics can be further imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following can used as a base stock in the present lubricating oil as well: (1) one or more Gas-to-Liquids (GTL) materials; and (2) hydrodewaxed, hydroisomerized, solvent dewaxed, or catalytically dewaxed base stocks derived from synthetic wax, natural wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks can include linear or branched hydrocarbyl compounds of C20 or higher, including C30 or higher.

The present lubricating oil compositions can include one or more Group I, II, III, IV, or V base stocks in addition to the neo-acid-derived ester base stock. In an aspect, Group I base stocks, if any, are present at a relatively low concentration if a high quality lubricating oil is desired. Group I base stocks can be introduced as a diluent of an additive package at a small quantity. Groups II and III base stocks can be included in the lubricating oil compositions, including those with high quality, e.g., those having a VI from 100 to 120. Group IV and V base stocks, including those of high quality, are also included into the present lubricating oil compositions.

Lubricating Oil Additives

The present lubricating oil composition can additionally contain one or more of the commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N.J. (1973); (iii) "Synthetics, Mineral Oils, and Bio-Based Lubricants," Edited by L. R. Rudnick, CRC Taylor and Francis, 2006, ISBN 1-57444-723-8; (iv) "Lubrication Fundamentals", J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalpha-olefins, " L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Colum 39, line 68; (c) U.S. Pat. No. 9,422,497 B2, Column 34, line 4 to Colum 40, line 55; and (d) U.S. Pat. No. 8,048,833 B2, Column 17, line 48 to Colum 27, line 12, the disclosures of which are incorporated herein in their entirety. These additives are commonly delivered with varying amounts of diluent oil that can range from 5 wt % to 50 wt % based on the total weight of the additive package before incorporation into the formulated oil. The additives useful in this disclosure do not have to be soluble in the lubricating oil compositions. Insoluble additives in oil can be dispersed in the present lubricating oil compositions.

When lubricating oil compositions contain one or more of the additives discussed above, the additive(s) are blended into the lubricating oil composition in an amount sufficient for it to perform its intended function.

It is noted that many of the additives are shipped from the additive manufacturer as a concentrate, containing one or more additives together, with a certain amount of base oil diluents.

Method for Making the Ester Products Comprising the Present Neo-Alcohol-Derived Ester Compounds and Lubricating Oil Base Stock Comprising the Same Provided herein are methods for making an ester product (such as a lubricating oil base stock) containing a compound defined by the structural Formula F-I as follows:

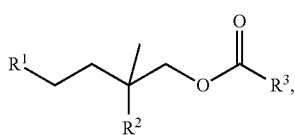

where $R^1$ and $R^2$ are each independently a hydrocarbyl group containing at least two (2) carbon atoms (such as a C2 to C60 hydrocarbyl group, a C2 to C60 alkyl group, a C2 to C60 linear or branched alkyl group, or a C2 to C30 linear or branched alkyl group; and $R^3$ is a glycol ether or a polyglycol ether.

The present methods comprise the steps of:
providing a neo-alcohol defined by the structural Formula F-II as follows:

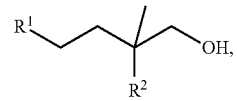

wherein $R^1$ and $R^2$ are the same as the $R^1$ and $R^2$ in Formula F-I, respectively;
reacting the neo-alcohol with an acid defined by the structural Formula F-III as

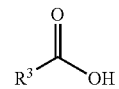

where $R^3$ is the same as the $R^3$ in Formula F-I, and/or an anhydride of the acid, in the presence of an acid catalyst to obtain a product mixture; and
obtaining the ester compound and/or the lubricating oil base stock from the product mixture.

It is desirable that the acid/anhydride used in the reaction comprises a single mono-acid for the purpose of making a single compound defined by the structural Formula F-I, or an ester product (such as a lubricating oil base stock) containing one or more compound(s) of the Formula F-I, although those of multiple acids can be used as well, especially for the purpose of making an ester product or a lubricating oil base stock which can comprise a mixture of multiple, different compounds each having a molecular structure represented by Formula F-I.

For a compound of the Formula F-I as defined herein, $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48 50, 52, 54, 56, 58, or 60, as long as c1<c2. In an aspect, c1 and c2 can define a range selected from any one of c1=2 and c2=30, c1=2 and c2=24, and c1=4 and c2=16. In an aspect, $R^1$ and $R^2$ each independently contain even number of carbon atoms.

At least one of $R^1$ and $R^2$ (or both $R^1$ and $R^2$ independently each) can be a branched alkyl group, such as a branched alkyl group defined by the structural Formula F-IV:

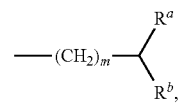

where $R^a$ and $R^b$ are independently hydrocarbyl groups, alkyl groups, linear or branched alkyl groups, or linear alkyl groups, m is a non-negative integer, including an integer satisfying an inequality selected from a group of m≥2, m≥3, m≥4 m≥5, m≥6, and m≥7. $R^a$ and $R^b$ can include, independently, c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48 50, 52, 54, 56, or 57, as long as c3<c4. In an aspect, c3 and c5 can be a pair of values selected from any one of c3=1 and c4=50, c3=1 and c4=40, c3=1 and c4=20, c3=1 and c4=16, and c3=1, and c4=10. In an aspect, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (or both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. In an aspect, the total number of carbon atoms in linear $R^1$ and $R^2$ is an even number. In an aspect, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. In an aspect, the total number of carbon atoms in the linear $R^1$ and $R^2$ combined is within a range selected from any one of 8 to 96, 8 to 80, 8 to 64, still more 8 to 48, 8 to 40, 8 to 32, 8 to 28, 8 to 26, 8 to 24, 8 to 22, and 8 to 20.

In an aspect, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. In an aspect, the total number of carbon atoms in $R^1$ and $R^2$ is in a range selected from any one of 8 to 96, more 8 to 80, 8 to 64, 8 to 48, 8 to 40, 8 to 32, 8 to 28, 8 to 26, 8 to 24, 8 to 22, and 8 to 20.

In an aspect, $R^1$ and $R^2$ are identical. In such case, $R^1$ and $R^2$ can contain even number of carbon atoms. In an aspect, $R^1$ and $R^2$ are identical linear alkyl groups. Where $R^1$ and $R^2$ differ, the groups can differ in terms of molar mass thereof by a gram per mole value less than any range endpoint selected from a group of 145, 130, 115, 100, 85, 70, 55, 45, 30, and 15. In an aspect, $R^1$ and $R^2$ can differ in terms of total number of carbon atoms contained therein by less than a range endpoint selected from a group of 10, 9, 8, 7, 6, 5, 4, 3, 2, and 1.

In an aspect, $R^3$ can be a glycol ether defined by the structural formula:

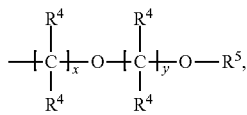

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10 and y is a value from about 1 to about 10.

In an aspect, $R^3$ can be a polyglycol ether defined by the structural formula:

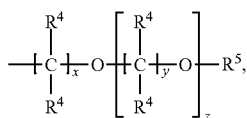

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, y is a value from about 1 to about 10, and z is a value from about 0 to about 100.

In an aspect, $R^3$ can include up to 60, 50, 40, 30, or 20 carbon atoms. In an aspect, $R^3$ is a C1-C24 group including carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2.

Methods for making the present ester products comprise the steps of: providing a neo-acid product containing a neo-acid compound defined by the structural Formula F-IIa as follows:

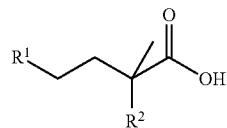

and contacting the neo-acid product with a reducing agent under reducing conditions.

The neo-acid product containing a neo-acid of the Formula F-II can be made by a method that includes the steps of providing a vinylidene olefin feed containing a vinylidene olefin defined by the structural Formula F-V:

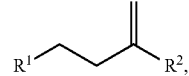

where $R^1$ and $R^2$ correspond to the $R^1$ and $R^2$ in Formula F-I; contacting the vinylidene olefin with carbon monoxide in a reactor in the presence of an acid catalyst (such as at a carbon monoxide partial pressure is at least one selected from a group of 1.0 MPa, 3.5 MPa, and 5.0 MPa) to obtain a reaction mixture; contacting the reaction mixture with water to obtain an acid product mixture; and obtaining at least a portion of the neo-acid product from the crude acid mixture.

The vinylidene olefin feed can be advantageously made from a terminal olefin monomer feed comprising the steps of providing a monomer feed containing a terminal olefin of the structural Formula F-VI and a terminal olefin of the structural Formula F-VII as follows:

$R^1$—CH=CH$_2$ (F-VI);

$R^2$—CH=CH$_2$ (F-VII);

where $R^1$ and $R^2$ correspond to the $R^1$ and $R^2$ in Formulas F-V, F-II and F-I, respectively; oligomerizing the monomer feed in an oligomerization reactor in the presence of a catalyst system containing a metallocene compound to obtain an oligomerization product mixture; and obtaining at least a portion of the vinylidene olefin feed from the oligomerization product mixture. In this method where $R^1$ and $R^2$ of Formula F-I are identical, a single terminal olefin of the structural Formula F-VI is used in the monomer feed.

Where $R^1$ and $R^2$ for Formula F-I are different, at least two terminal olefin having different Formula F-VI and F-VII are used in the monomer feed. In case two different terminal olefins are used in the monomer feed, the oligomerization product mixture can include up to four vinylidene olefins as dimers of the two terminal olefins, which can be separated to obtain the desirable vinylidene olefin feed including one, two, three, or all four vinylidene olefins. Nine vinylidene olefin dimers can result from three different terminal olefins in the monomer feed. These different vinylidene olefins, if contained in the vinylidene olefin feed of the method for making the neo-alcohol described above, can be converted into corresponding neo-alcohols in the neo-alcohol product, which, in turn, can be converted into corresponding ester compounds in the neo-alcohol-derived ester product.

The above methods for making neo-alcohol product starting from terminal olefin monomer via the vinylidene olefin intermediate can be illustrated in the following Scheme-I.

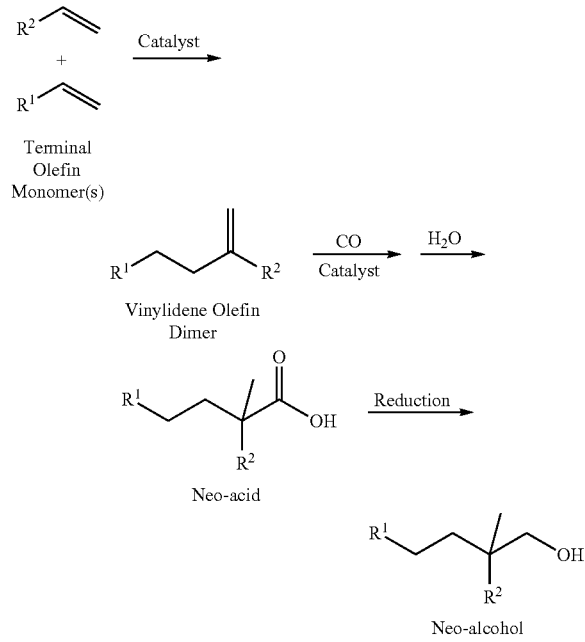

Only one type of vinylidene olefin dimer is illustrated in Scheme-I above. Specific examples of Scheme-I are provided in the example section below. Co-pending, co-assigned U.S. Provisional Patent Application No. 62/565,501, entitled "Neo-Alcohol Compounds, Processes for Making Same and Use Thereof" and having a filing date of Sep. 29, 2017/discloses neo-alcohols suitable for making the esters of this disclosure, and processes for making such neo-alcohols, the content of which is incorporate herein by reference in its entirety. Co-pending, co-assigned U.S. Provisional Application Ser. No. 62/565,560, entitled "Neo-Acids and Process for Making the Same" and having a filing date of Sep. 29, 2017 discloses neo-acids suitable for use in the process for making neo-alcohols and processes for making neo-acids, the content of which is incorporated herein by reference in its entirety.

Co-assigned U.S. Provisional Application Ser. No. 62/551,081 entitled "Process for Making Vinylidene Olefin" and having a filing date of Aug. 28, 2017, discloses vinylidene olefin dimers of terminal olefins useful for making neo-acids suitable for making neo-alcohols, and processes for making such vinylidene dimers, the content of which is incorporated herein by reference in its entirety.

Non-limiting examples of neo-alcohols useful in the methods of this disclosure include the following: 2-ethyl-2-methylhexan-1-ol; 2-methyl-2-propylheptan-1-ol; 2-butyl-2-methyloctan-1-ol; 2-methyl-2-pentylnonan-1-ol; 2-hexyl-2-methyldecan-1-ol; 2-heptyl-2-methylundecan-1-ol; 2-methyl-2-octyldodecan-1-ol; 2-decyl-2-methyltetradecan-1-ol; 2-dodecyl-2-methylhexadecan-1-ol; 2-methyl-2-tetradecyloctadecan-1-ol; and 2-methyl-2-hexadecylicosan-1-ol.

In the carboxylic acid of the Formula F-III, $R^3$ corresponds to the $R^3$ of the Formula F-I as described above.

In the method for making the ester of this disclosure, either the carboxylic acid of the Formula F-III, or its anhydride, or a mixture thereof, can be used to react with the neo-alcohol of the Formula F-II.

Examples of carboxylic acids useful in methods of the present disclosure include glycol ether acids such as methoxyacetic acid, methoxypropionic acid, methoxyethoxyacetic acid, methoxyethoxyethoxyacetic acid, ethoxyacetic acid, ethoxyethoxyacetic acid, ethoxyethoxyethoxyacetic acid, propoxyacetic acid, propoxyethoxyacetic acid, propoxyethoxyethoxyacetic acid, butoxyacetic acid, butoxyethoxyacetic acid, butoxyethoxyethoxyacetic acid, propoxybenzoic acid, and the like.

Illustrative compounds having a chemical structure of Formula F-III can also include compounds prepared from a reaction of functionalized carboxylic acid, such as a hydroxy acid or haloacid, and a glycol ether alcohol, where the glycol ether alcohol can include, for example, methoxyethanol, ethoxyethanol, propoxyethanol, butoxyethanol, pentoxyethanol, hexyloxyethanol, phenoxyethanol, diethylene glycol methyl ether, diethylene glycol ethyl ether, diethylene glycol propyl ether, diethylene glycol butyl ether, diethylene glycol pentyl ether, diethylene glycol hexyl ether, diethylene glycol benzyl ether, triethylene glycol methyl ether, triethylene glycol ethyl ether, triethylene glycol propyl ether, triethylene glycol butyl ether, triethylene glycol pentyl ether, triethylene glycol hexyl ether, triethylene glycol benzyl ether, tetraethylene glycol methyl ether, tetraethylene glycol ethyl ether, tetraethylene glycol propyl ether, tetraethylene glycol butyl ether, tetraethylene glycol pentyl ether, tetraethylene glycol hexyl ether, tetraethylene glycol benzyl ether, propylene glycol methyl ether, propylene glycol ethyl ether, propylene glycol propyl ether, propylene glycol butyl ether, propylene glycol hexyl ether, propylene glycol benzyl ether, dipropylene glycol methyl ether, dipropylene glycol propyl ether, dipropylene glycol butyl ether, dipropylene glycol pentyl ether, dipropylene glycol hexyl ether, dipropylene glycol benzyl ether, and the like.

In an aspect, a single carboxylic acid or its anhydride of the Formula F-III and a single neo-alcohol can be used in the esterification reaction to produce an ester product containing a single ester compound of this disclosure and/or a lubricating oil base stock containing a single ester compound. In such case, if an acid/anhydride of a single mono-acid is used, a high-purity ester compound of the Formula F-I can be obtained and used as a lubricating oil base stock. This is illustrated in example section below.

It is also contemplated that multiple carboxylic acids and/or multiple neo-alcohols can be used in the esterification reaction. In such cases multiple ester compounds will be produced. The ratio between the quantities of multiple ester compounds can change as a function of the ratio between the quantities of the multiple neo-alcohols and/or multiple acids used. In certain situations, such as when a mixture of neo-alcohols having similar molecular weights and structures and/or a mixture of carboxylic acids having similar molecular weights and structures can be procured at a lower cost than a pure neo-alcohol product or a pure carboxylic acid product, this embodiment can be highly economic to produce a mixture of ester compounds with similar molecular structures, molecular weights, and properties suitable as a lubricating oil base stock product.

The anhydrides of the carboxylic acid can be prepared from a corresponding acid of Formula F-III by, e.g., dehydration, if not directly available commercially. Dehydration can be achieved by, e.g., reacting with dehydration agents such as $P_2O_5$, followed by separation.

The catalyst used in the reaction can be an acid, desirably a strong acid. Non-limiting examples of such acid are: p-toluenesulfonic acid monohydride ("PTSA"), titanium isopropoxide and sulfuric acid.

The reaction can be conveniently carried out in the presence of a solvent. The specific solvent used is not critical as long as it is inert in the reaction. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

Reaction conditions for the reaction of the neo-alcohol with one or more acids or anhydrides, such as temperature, pressure and contact time, can also vary greatly and any suitable combination of such conditions can be employed herein. The reaction temperature can range between any range selected from a group of about 25° C. to about 250° C., about 30° C. to about 200° C., and about 60° C. to about 150° C. The reaction can be carried out under ambient pressure and the contact time can vary from a matter of seconds or minutes to a few hours or greater. The reactants can be added to the reaction mixture or combined in any order. The stir time employed can be a range selected from one of about 0.5 to about 48 hours, about 1 to 36 hours, and about 2 to 24 hours.

The reaction mixture from the esterification reaction can include the intended ester product(s), water, and one or more of unreacted acid/anhydride and neo-alcohol, and byproducts such as ethers and esters of the acid catalyst. Continuous removal of water from the reaction system can result in higher yield of the ester product. Components in the reaction mixture having a boiling point lower than the intended neo-alcohol-derived ester can be removed by flashing. Depending on the reactants used and reaction conditions, purification methods such as solvent extraction, chromatography, distillation, and the use of sorbents can be carried out to remove byproducts from reaction mixture to finally obtain an ester product of this disclosure containing a single compound of the Formula F-I or a mixture of multiple compounds of Formula F-I, which can be used as a base stock product, or combined with other, similar compounds to form a base stock product. In an aspect, the neo-alcohol-derived ester product obtainable from the present methods comprise one or more neo-alcohol-derived ester compounds.

In an aspect, the neo-alcohol-derived ester product obtainable from the present methods include neo-alcohol-derived ester compounds at a total concentration thereof, based on the total weight of the neo-alcohol-derived ester product, of at least 95 wt %, at least 98 wt %, or at least 99 wt %. In an aspect, the neo-alcohol-derived ester product obtainable from the methods comprises one predominant neo-alcohol-derived ester compound. In an aspect, the neo-alcohol-derived ester product obtainable from the present method comprises a predominant neo-alcohol-derived ester compound at a concentration thereof, based on the total weight of the neo-alcohol-derived ester product, of at least 95 wt %, at least 98 wt %, or at least 99 wt %.

In an aspect, the C6-C11 and C12-C18 neo-alcohols produced by the present methods can be used as "plasticizer alcohols" and "detergent alcohols," respectively.

This disclosure is further illustrated by the following non-limiting examples.

EXAMPLE

In the following example, kinematic viscosity at 100° C. ("KV100") and 40° C. ("KV40") of fluids were determined pursuant to ASTM standards D-445; viscosity index ("VI") was determined pursuant to ASTM standard D-2270; and Noack volatility ("NV") were determined using thermal gravimetric analysis ("TGA").

By changing the glycol ether component of a neo-alcohol-derived ester compound, the overall polarity of fluids treated with such compounds can be modified. For example, the polarity of a neo-alcohol-derived ester can be modified by varying the $R^3$ glycol ether group of Formula F-I with any number of synthetic and/or commercially available glycol ethers. For example, glycol ethers such as di(ethylene glycol) monohexyl ether, tri(ethylene glycol) monomethyl ether, tri(propylene glycol) monomethyl ether, tri(ethylene glycol) monoethyl ether, tri(ethylene glycol) monobutyl ether, di(ethylene glycol) monoethyl ether, di(ethylene glycol) monobutyl ether, tri(propylene glycol) monopropyl ether, tri(propylene glycol) monobutyl ether, poly(ethylene glycol) dodecyl ether (Brij 30), and ethylene glycol mono-2-ethylhexyl ether can be used. Glycol ethers, having both ether and alcohol functional groups in the same molecule, represent a versatile class of organic solvents. Glycol ether products are produced through continuous processes of selectively reacting an alcohol (ethanol, butanol, hexanol) with ethylene oxide. Diethylene glycol monohexyl ether ($C_6H_{13}(OCH_2CH_2)_2OH$, Hexyl CARBITOL Solvent) displays a strong hydrocarbon-type solvency.

Example 1

Synthesis of 2-methyl-2-octyldodecyl 2-(2-methoxyethoxy)acetate

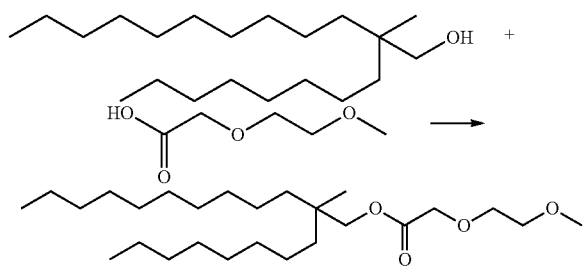

2-methyl-2-octyldodecan-1-ol (5 g, 0.0160 mol, MW 312.34), 2-(2-methoxyethoxy) acetic acid (3.22 g, mole 0.0448, MW 134.13) and p-toluenesulfonic acid monohydride (PTSA) (1.52 g, 0.0080 mol, MW 190.22) were mixed 75 mL toluene in three necked round bottom flask along with a dean-stark apparatus. Then solution was reflux for overnight (18 h). In 18 hours, ~2-3 mL water was collected in the trap. Toluene was removed by simple distillation at 50° C. The extracted product in methylene chloride washed with water (1×100 mL) and 10% $NaHCO_3$ (1×100 mL). Evaporated the methylene chloride and fallowed by flash chromatography with hexane. The Hexane layer is removed by roto-vap at 60° C. under vacuum and high boiling components by air bath oven at 190° C. The isolated product was characterized by IR, $^1$HNMR, $^{13}$CNMR. Yields: 4.5 g (66%). IR (cm$^{-1}$): 2924.63, 2853.19, 1758.69, 1737.54, 1467.06, 1377.99, 12.78.47, 1198.54, 1147.94, 1124.9, 1017.96, 854.37, and 721.72.

Example 2

Lube Properties of the Base Stock

The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The products were evaluated as synthetic base stocks.

The ester fluid was evaluated as synthetic base stock and results are shown in Table 2.

TABLE 2

| Example # | MW | Kv$_{100}$ cSt | Kv$_{40}$ cSt | VI | Noack (TGA) |
|---|---|---|---|---|---|
| 1 | 428 | 6.13 | 33.3 | 133 | 9.5 |

Example 3

Specific Heat Capacity of Glycol Ether Fluids

In addition to lubrication applications, base stock fluids and circulating fluids can also function to transfer heat from high temperature zones. In lubricated systems, examples of heat sources that are often controlled by cooling systems include: heat generated by combustion processes, heat resulting from friction within a lubricated contact, heat created by energy sources, and heat used in manufacturing processes (e.g., paper and steel making).

In some cases, specialized fluids are used for the sole purpose of removing heat from high temperature zones. Examples include coolants used in internal combustion engine applications, and transformer oils used to cool electrical distribution equipment. Formulations containing glycol ether esters of neo-alcohols in accordance with the present disclosure can also meet the requirements for cooling systems to cool battery and power generation systems in electric and hybrid vehicles to dissipate and distribute heat.

Base stock fluids in accordance with the present disclosure formulated as lubricating and/or cooling fluids can remove heat via combinations of conductivity and convection mechanisms. The heat removed can be a function of: fluid properties, such as heat capacity and thermal conductivity; system design, such as selection of materials that determine the heat flow across fluid/surface interfaces; and operational factors, such as fluid flow rate and temperature difference between fluid and the high temperature zone requiring cooling.

In this example the specific heat capacity of the samples was measured and evaluated against a comparative commercial base stock formulation. Results are shown in Table 3.

TABLE 3

Specific Heat Capacity (J/g/° C.) of Base Stocks

| Temp ° C. | Example 1 | Comparative |
|---|---|---|
| 20 | 2.08 | 1.46 |
| 40 | 2.14 | 1.52 |
| 60 | 2.20 | 1.57 |

The invention claimed is:
1. A compound of the structural Formula F-I:

wherein $R^1$ and $R^2$ are independently each a hydrocarbyl group comprising at least 2 carbon atoms; and $R^3$ is a glycol ether or a polyglycol ether.

2. The compound of claim 1, wherein $R^1$ and $R^2$ are each independently a C2 to C30 linear or branched alkyl group.

3. The compound of claim 1, wherein at least one of $R^1$ and $R^2$ is a linear alkyl group.

4. The compound of claim 3, wherein at least one of $R^1$ and $R^2$ is selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

5. The compound of claim 4, wherein at least one of $R^1$ and $R^2$ is selected from n-butyl, n-hexyl, n-octyl, n-decyl, and n-dodecyl.

6. The compound of claim 1, wherein $R^1$ and $R^2$ are independently each a linear alkyl group.

7. The compound of claim 1, wherein at least one of $R^1$ and $R^2$ is a branched alkyl group.

8. The compound of claim 7, wherein at least one of $R^1$ and $R^2$ is selected from ethylhexyl, 2-propylheptanyl, 2-butyloctyl, and 3,5-dimethyloctyl.

9. The compound of claim 1, wherein $R^1$ and $R^2$ are identical.

10. The compound of claim 1, wherein $R^3$ is a glycol ether of the structural formula:

wherein each $R^4$ is the same or different and is hydrogen or a substituted or unsubstituted alkyl group (C1-C30), alkenyl group (C2-C30), alkoxy group (C1-C30), aryl group (C6-C30), or arylalkyl group (C7-C30), $R^5$ is hydrogen or a substituted or unsubstituted alkyl group (C1-C30), alkenyl group (C2-C30), alkoxy group (C1-C30), aryl group (C6-C30), or arylalkyl group (C7-C30), x is a value from 0 to 10, and y is a value from 1 to 10.

11. The compound of claim 1, wherein $R^3$ is a polyglycol ether of the structural formula:

$$-\left[\begin{array}{c}R^4\\|\\C\\|\\R^4\end{array}\right]_x -O-\left[\left[\begin{array}{c}R^4\\|\\C\\|\\R^4\end{array}\right]_y -O\right]_z -R^5,$$

wherein each $R^4$ is the same or different and is hydrogen or a substituted or unsubstituted alkyl group (C1-C30), alkenyl group (C2-C30), alkoxy group (C1-C30), aryl group (C6-C30), arylalkyl group (C7-C30), $R^5$ is hydrogen or a substituted or unsubstituted alkyl group (C1-C30), alkenyl group (C2-C30), alkoxy group (C1-C30), aryl group (C6-C30), or arylalkyl group (C7-C30), x is a value from 0 to 10, y is a value from 1 to 10, and z is a value from 1 to 100.

12. The compound of claim 1, wherein the compound is one or more compounds selected from the group of 2-methyl-2-octyldodecyl 2-(2-methoxyethoxy)acetate, 2-methyl-2-octyldodecyl 2-(2-methoxyethoxy)acetate, 2-methyl-2-hexyldecyl 2-(2-methoxyethoxy)acetate, 2-methyl-2-octyldodecyl 2-(2-ethoxyethoxy)acetate, 2-methyl-2-octyldodecyl 2-(3-methoxypropoxy)acetate, 2-methyl-2-octyldodecyl 3-(2-methoxyethoxy)propionate, 2-methyl-2-octyldodecyl 2-(2-(2-methoxyethoxy)ethoxy)acetate, 2-methyl-2-octyldodecyl 2-(2-(2-methoxyethoxy)ethoxy)acetate, 2-methyl-2-hexyldecyl 2-(2-methoxyethoxy)ethoxy)acetate, 2-methyl-2-octyldodecyl 2-(2-(2-ethoxyethoxy)ethoxy)acetate, 2-methyl-2-octyldodecyl 2-(2-(3-methoxypropoxy)ethoxy)acetate, 2-methyl-2-octyldodecyl 2-(3-(2-methoxyethoxy)propoxy)acetate, and 2-methyl-2-octyldodecyl 3-(2-(2-ethoxyethoxy)ethoxy)propionate.

13. The compound of claim 1, wherein the compound is 2-methyl-2-octyldodecyl 2-(2-(2-methoxyethoxy)ethoxy)acetate or 2-methyl-2-octyldodecyl 2-(2-methoxyethoxy)ethoxy acetate.

14. A lubricating oil composition comprising a compound defined by the structural Formula F-I:

$$R^1 \diagdown \diagup \diagdown_{R^2}^{\diagup} \diagdown_O \diagdown \diagup \diagdown_{R^3}^{O},$$

wherein
$R^1$ and $R^2$ are independently each a hydrocarbyl group comprising at least 2 carbon atoms; and
$R^3$ is a glycol ether or a polyglycol ether.

15. A lubricating oil composition of claim 14, which is a lubricating oil formulation.

16. A lubricating oil composition of claim 14, wherein the lubricating oil composition is formulated as a coolant for an electric vehicle.

17. The lubricating oil composition of claim 14, having a kinematic viscosity at 100° C. as determined pursuant to ASTM D445 in the range from 1 to 140 cSt.

18. A method for making an ester compound of the structural Formula F-I:

$$R^1 \diagdown \diagup \diagdown_{R^2}^{\diagup} \diagdown_O \diagdown \diagup \diagdown_{R^3}^{O},$$

where $R^1$ and $R^2$ are independently each a hydrocarbyl group comprising at least two carbon atoms; and $R^3$ is a glycol ether or a polyglycol ether, the method comprising the steps of:

providing a neo-alcohol of the structural Formula F-II:

$$R^1 \diagdown \diagup \diagdown_{R^2}^{\diagup} \diagdown_{OH},$$

wherein $R^1$ and $R^2$ are the same as the $R^1$ and $R^2$ of Formula F-I, respectively;

reacting the neo-alcohol with an acid of the structural Formula II:

$$R^3 \diagdown \diagup \diagdown_{OH}^{O}$$

wherein $R^3$ is the same as the $R^3$ of Formula F-I, and/or an anhydride of the acid, in the presence of an acid catalyst to obtain a product mixture; and obtaining the ester compound from the product mixture.

19. The method of claim 18, wherein $R^1$ and $R^2$ are independently each a C2 to C30 linear or branched alkyl group.

20. The method of claim 18, wherein $R^1$ and $R^2$ are independently selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

21. The method of claim 18, wherein $R^3$ is a glycol ether of the structural formula:

$$-\left[\begin{array}{c}R^4\\|\\C\\|\\R^4\end{array}\right]_x -O-\left[\begin{array}{c}R^4\\|\\C\\|\\R^4\end{array}\right]_y -O-R^5,$$

wherein each $R^4$ is the same or different and is hydrogen or a substituted or unsubstituted alkyl group (C1-C30), alkenyl group (C2-C30), alkoxy group (C1-C30), aryl group (C6-C30), or arylalkyl group (C7-C30), $R^5$ is hydrogen or a substituted or unsubstituted alkyl group (C1-C30), alkenyl group (C2-C30), alkoxy group (C1-C30), aryl group (C6-C30), or arylalkyl group (C7-C30), x is a value from 0 to 10, and y is a value from 1 to 10.

22. The method of claim 18, wherein $R^3$ is a polyglycol ether of the structural formula:

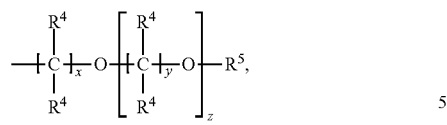

wherein each $R^4$ is the same or different and is hydrogen or a substituted or unsubstituted alkyl group (C1-C30), alkenyl group (C2-C30), alkoxy group (C1-C30), aryl group (C6-C30), or arylalkyl group (C7-C30), $R^5$ is hydrogen or a substituted or unsubstituted alkyl group (C1-C30), alkenyl group (C2 C30), alkoxy group (C1-C30), aryl group (C6-C30), or arylalkyl group (C7-C30), x is a value from 0 to 10, y is a value from 1 to 10, and z is a value from 1 to 100.

23. The method of claim 18, wherein the neo-alcohol is 2-ethyl-2-methylhexan-1-ol; 2-methyl-2-propylheptan-1-ol; 2-butyl-2-methyloctan-1-ol; 2-methyl-2-pentylnonan-1-ol; 2-hexyl-2-methyldecan-1-ol; 2-heptyl-2-methylundecan-1-ol; 2-methyl-2-octyldodecan-1-ol; 2-decyl-2-methyltetradecan-1-ol; 2-dodecyl-2-methylhexadecan-1-ol; 2-methyl-2-tetradecyloctadecan-1-ol; and/or 2-methyl-2-hexadecylicosan-1-ol; and/or mixtures and/or combinations thereof.

\* \* \* \* \*